United States Patent
Jones et al.

(10) Patent No.: US 8,496,735 B2
(45) Date of Patent: Jul. 30, 2013

(54) METHOD AND APPARATUS FOR CONTROL AND ELIMINATION OF UNDESIRABLE SUBSTANCES

(71) Applicant: Timilon Technology Acquisitions LLC, Naples, FL (US)

(72) Inventors: David Jones, San Jose, CA (US); Kyle Knappenberger, Topeka, KS (US); Lincoln Mertz, Manhattan, KS (US); Olga Koper, Dublin, OH (US); David Brotton, Manhattan, KS (US); Deborah Basco, Cape Coral, FL (US); Bill Sanford, Naples, FL (US)

(73) Assignee: Timilon Technology Acquisitions LLC, Naples, FL (US)

( * ) Notice: Subject to any disclaimer, the term of this patent is extended or adjusted under 35 U.S.C. 154(b) by 0 days.

(21) Appl. No.: 13/654,052

(22) Filed: Oct. 17, 2012

(65) Prior Publication Data

US 2013/0036908 A1 Feb. 14, 2013

Related U.S. Application Data

(63) Continuation of application No. 12/548,060, filed on Aug. 26, 2009, now abandoned.

(60) Provisional application No. 61/091,980, filed on Aug. 26, 2008.

(51) Int. Cl.
*B01D 53/04* (2006.01)
*A61L 9/16* (2006.01)

(52) U.S. Cl.
USPC ............. 95/141; 96/138; 96/142; 96/154; 55/524

(58) Field of Classification Search
USPC ...... 96/134, 135, 138, 142, 151, 154; 95/141, 95/135; 55/524, 527; 428/117; 977/773, 775, 977/777, 811, 903; 422/5, 120
See application file for complete search history.

(56) References Cited

U.S. PATENT DOCUMENTS

| | | | |
|---|---|---|---|
| 5,665,143 | A | 9/1997 | Jarvis et al. |
| 5,712,219 | A | 1/1998 | Klabunde et al. |

(Continued)

FOREIGN PATENT DOCUMENTS

| | | | |
|---|---|---|---|
| JP | 2000-135418 A | | 5/2000 |
| KR | 10-2005-0096514 A | | 10/2005 |

(Continued)

OTHER PUBLICATIONS

Examination Report for NZ Patent Application Serial No. 568556, dated Feb. 3, 2010 (2 pgs).

(Continued)

*Primary Examiner* — Frank Lawrence, Jr.
(74) *Attorney, Agent, or Firm* — Hovey Williams LLP

(57) ABSTRACT

Apparatus and methods for reducing or eliminating undesirable air-borne substances, such as odors, bacteria, viruses, fungi, and toxins, are provided. A filter containing nanocrystalline metal oxide or metal hydroxide particles may be installed within an air handling apparatus such as an existing HVAC unit located within a building, and particularly within a home, or a portable air processor or purifier. The air handling apparatus comprises a blower which pulls air containing various undesirable substances from within the enclosed environment and directs it through a filtering device containing the nanocrystalline particles. The undesirable substances are sorbed by the nanocrystalline particles thereby creating a deodorized stream of air that may then be directed back into various portions of the enclosed environment or vented to the atmosphere.

20 Claims, 5 Drawing Sheets

U.S. PATENT DOCUMENTS

| | | | |
|---|---|---|---|
| 5,759,939 | A | 6/1998 | Klabunde et al. |
| 5,914,436 | A | 6/1999 | Klabunde et al. |
| 6,057,488 | A | 5/2000 | Koper et al. |
| 6,087,294 | A | 7/2000 | Klabunde et al. |
| 6,093,236 | A | 7/2000 | Klabunde et al. |
| 6,417,423 | B1 | 7/2002 | Koper et al. |
| 6,653,519 | B2 | 11/2003 | Koper et al. |
| 6,843,919 | B2 | 1/2005 | Klabunde et al. |
| 6,860,924 | B2 | 3/2005 | Rajagopalan et al. |
| 6,887,302 | B2 | 5/2005 | Rajagopalan et al. |
| 7,029,516 | B2 | 4/2006 | Campbell et al. |
| 7,256,156 | B2 | 8/2007 | Axtell et al. |
| 7,335,808 | B2 | 2/2008 | Koper et al. |
| 7,341,977 | B2 | 3/2008 | Klabunde et al. |
| 7,661,483 | B2 | 2/2010 | Mulukutla et al. |
| 2004/0118285 | A1 | 6/2004 | Kim et al. |
| 2004/0258581 | A1 | 12/2004 | Wei et al. |
| 2005/0084464 | A1 | 4/2005 | McGrath et al. |
| 2008/0210902 | A1 | 9/2008 | Coy et al. |
| 2009/0098016 | A1 | 4/2009 | Koper et al. |

FOREIGN PATENT DOCUMENTS

| | | |
|---|---|---|
| KR | 10-2008-0059959 A | 7/2008 |
| WO | 03093734 A1 | 11/2003 |
| WO | 2007041553 A1 | 4/2007 |
| WO | 2007051145 A2 | 5/2007 |

OTHER PUBLICATIONS

PCT International Search Report dated Apr. 2, 2010 re Application No. PCT/US2009/055078, filed Aug. 26, 2009; Applicant—NanoScale Corporation (3 pages).

PCT International Written Opinion dated Apr. 2, 2010 re Application No. PCT/US2009/055078, filed Aug. 26, 2009; Applicant—NanoScale Corporation; (6 pages).

European Search Report for Application No. 09812050.4, dated Oct. 22, 2012, 11 pages.

METHOD AND APPARATUS FOR CONTROL AND ELIMINATION OF UNDESIRABLE SUBSTANCES

RELATED APPLICATIONS

The present application claims the benefit of U.S. Provisional Patent Application No. 61/091,980, entitled METHOD AND APPARATUS FOR ODOR CONTROL AND ELIMINATION, filed Aug. 26, 2008, which is incorporated herein by reference in its entirety. The present application is also a continuation of U.S. patent application Ser. No. 12/548,060, filed Aug. 26, 2009, and now abandoned which is incorporated herein by reference in its entirety.

BACKGROUND OF THE INVENTION

1. Field of the Invention

The present invention generally pertains to methods of treating undesirable substances such as malodors, viruses, bacteria, fungi, and toxins, particularly those undesirable substances present within enclosed environments, including homes, vehicles and other types of permanent and mobile structures, using nanocrystalline metal oxide and metal hydroxide particles that are contained within a filter apparatus. The filter apparatus may be adapted for use with existing heating, ventilation, and air conditioning (HVAC) equipment present in a home or vehicle, or in a portable air purification unit or processor.

2. Description of the Prior Art

Common sources of malodors include smoke/tobacco, human and pet excrements, mold and mildew, bacteria, food, beverages (spoiled milk), vomit, and dirty clothes. Although malodors have a multitude of different sources, chemically speaking, most malodors are organic (carbon containing compounds) in nature. Malodors, can easily permeate, penetrate, impregnate and cling to surfaces within enclosed environments such as homes and buildings.

Various types of odor problems occur in homes. Some of the leading causes of nuisance odors are the result of the biological contamination. When these microbial organisms decay and rot, they give off gases and noxious fumes. Unfortunately these are not just aesthetic problems. Health concerns ranging from nausea to death can arise from acute and repeated exposure to these and other odor causing compounds. Indoor air pollution is now considered by the EPA and Congress to be America's No. 1 environmental health problem. It is estimated that 4-5 million Americans already suffer from the effects of chemically induced environmental illnesses. Tightly sealed buildings and homes may be more energy efficient but can trap pollutants and microbes indoors causing allergies, odors, mold, and illness.

Furthermore, the EPA conducted a 17-year study and found that women working in their homes had a 55% greater risk of dying from cancer than those who worked in an office, primarily due to the use of ordinary household cleaners. Some of the products found in American homes have chemical ingredients that are potentially harmful. These products include oven cleaners, paint removers, pesticides, solvents, drain cleaners, and more.

Treatment of malodors is generally approached in two ways: masking or elimination. If odor masking is used, the source of the malodor is not eliminated and will eventually return once the "masking" agent is removed. In many cases, the malodor is so overpowering that a masking agent is ineffective. Treatment by elimination, on the other hand, removes the malodor by removing its source. Elimination can be done by physically replacing the contaminated surface or by removing the malodor-causing agent itself.

Numerous compositions and methods have been developed for reducing odors from a variety of sources; however, they have had only limited success because the odors associated with a wide range of sources are complex and can comprise a mixture of different substances including, but not limited to inorganic bases such as ammonia, organic acids such as butyric acid and isovaleric acid, and neutral molecules such as acetaldehyde and methyl mercaptan. The most common ways of reducing malodors caused by these substances include: (i) masking the odor using an odor-masking aroma, (ii) adsorption of the odor using inorganic materials, such as activated carbon, sodium bicarbonate, and talcum powder, and (iii) using a composite, such as chlorine dioxide, for reducing bacteria which produce the malodorous substances. However, these methods present the following problems: (i) the odor is not eliminated, but only masked, (ii) the adsorption capability of these traditional sorbents is limited, (iii) by using the oxidizing agent, a secondary pollutant can be produced, and (iv) the sorbents can be effective only under certain conditions such as a wet environment.

As noted above, a number of odors can be produced from bacteria or other microorganisms. Removal or elimination of these microorganisms can be useful in permanent odor elimination. Further, enclosed environments including hospitals, homes, schools, and airplanes can harbor viruses, bacteria, fungi and toxins for transmission among people located therein. Elimination or control of these substances from the air within the enclosed space can greatly reduce the incidence of transmission and illnesses associated therewith.

SUMMARY OF THE INVENTION

The present invention is generally directed toward novel filter apparatus and its use in the control and elimination of undesirable substances, such as odors, bacteria, viruses, fungi, and toxins, from within enclosed environments such as homes, office buildings, industrial buildings, vehicles, and the like. In one embodiment, there is provided a system for controlling and eliminating undesirable substances in an enclosed environment. The system generally comprises air handling apparatus including a blower that acts as a motive force for circulating air within the enclosed environment, and an air filtration device positioned so as to come into contact with air being circulated within the enclosed environment by the air handling apparatus. The filtration device comprises nanocrystalline metal oxide or metal hydroxide particles capable of removing one or more undesirable substances from the air flowing through the air handling apparatus.

In certain embodiments, the air handling apparatus includes a filter cartridge that is removably inserted into the air handling apparatus and disposed transversely with respect to the flow of air through the air handling apparatus. In certain applications, such as in an HVAC unit, the filter cartridge is disposed generally perpendicular to the local direction of air flow through the air handling apparatus. The filter cartridge comprises first filter media for removing undesirable substances such as bacteria, viruses, fungi, toxins and odors, from the air flowing through the air handling apparatus. The first filter media comprises nanocrystalline metal oxide or metal hydroxide particles capable of removing one or more undesirable substances from the air flowing through the air handling apparatus. In certain embodiments, the filter cartridge may also include second filter media for removing particulate matter from the air flowing through the air handling apparatus.

In another embodiment according to the present invention, there is provided a method of controlling and eliminating undesirable substances from within an enclosed environment. The method utilizes an air handling apparatus including a blower that acts as a motive force for circulating air within the enclosed environment and is located within the enclosed environment. The method generally comprises providing an air filtration device positioned so as to come into contact with air being circulated within the enclosed environment by the air handling apparatus, and using the blower to direct air containing at least one undesirable substance through the filtration device in order to remove at least a portion of the at least one undesirable substance from the air thereby producing a flow of purified air. The filtration device comprises nanocrystalline metal oxide or metal hydroxide particles capable of removing at least one undesirable substance from the air flowing through the air handling apparatus.

DETAILED DESCRIPTION OF THE PREFERRED EMBODIMENT

Figure 1:
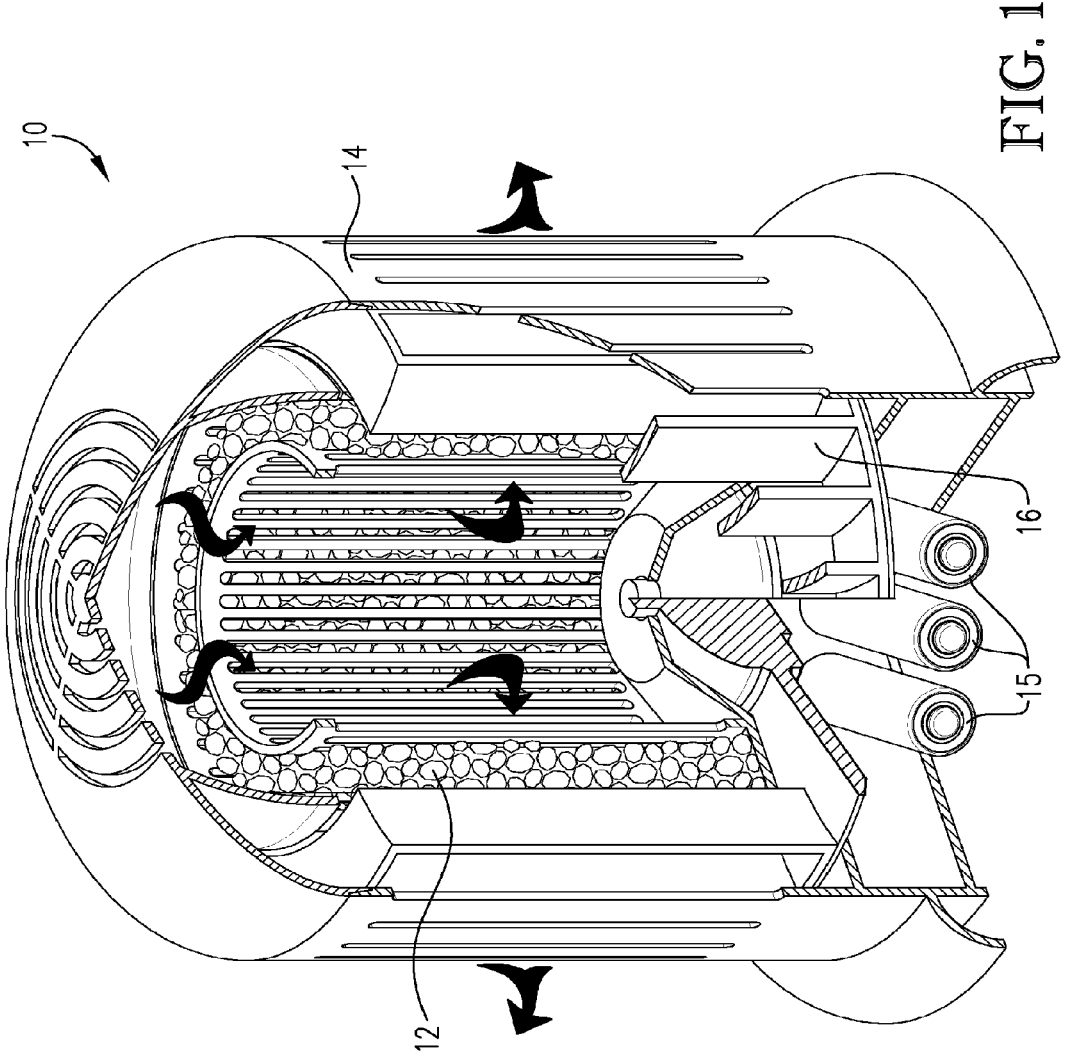
FIG. 1 is a view of a portable air purifier utilizing nanocrystalline particles according to the present invention.

The present invention is generally directed toward the use of nanocrystalline materials, particularly nanocrystalline metal oxides and hydroxides in systems for controlling and eliminating undesirable substances from air. Such undesirable substances include odors and airborne pathogens like viruses, bacteria, toxins, and fungi. The present invention is particularly suited for use in both mobile environments (such as vehicles, boats, trains, airplanes, and the like) and stationary environments (such as buildings with an existing HVAC unit installed therein or having a portable air processing device or air purifier located therein). The use of nanocrystalline metal oxides and hydroxides in sorbing odors is described in co-pending U.S. patent application Ser. No. 12/091,671 entitled TREATMENT OF ODORS USING NANOCRYSTALLINE METAL OXIDES, published as U.S. Patent Application Publication 2009/0098016, which is incorporated by reference herein in its entirety.

The nanocrystalline materials may comprise nanocrystalline metal oxides and hydroxides, coated metal oxides/hydroxides (i.e., halogen coatings), doped metal oxides/hydroxides, surfactant coated nanocrystalline metal oxides and combinations thereof. The terms "metal oxides" and "metal hydroxides" as used herein collectively refer to all such materials that comprise, preferably as the principal constituent, a metal oxide or metal hydroxide material. Preferred nanocrystalline materials for use in connection with the present invention include the metal oxides and metal hydroxides of Mg, Sr, Ba, Ca, Ti, Zr, Fe, V, Mn, Ni, Cu, Al, Si, Zn, Ag, Mo, Sb, Cr, Co and mixtures thereof. Additional preferred nanocrystalline materials include coated nanocrystalline materials such as those disclosed in U.S. Pat. Nos. 6,093,236, and 5,759,939 (metal oxide coated with another metal oxide), halogenated particles such as those disclosed in U.S. Pat. Nos. 6,653,519, 6,087,294 and 6,057,488 (nanocrystalline materials having reactive atoms stabilized on the surfaces thereof, the reactive atoms including oxygen ion moieties, ozone, halogens, and group I metals), doped metal oxides and hydroxides such as silver doped alumina, intimately mixed metal oxides such as combinations of Mg, Al, and Ti, carbon coated metal oxides, and air stable nanocrystalline materials such as those described in U.S. Pat. Nos. 6,887,302 and 6,860,924 (nanocrystalline materials coated with a surfactant, wax, oil, silyl, synthetic or natural polymer, or resin), all of which are incorporated by reference herein. The nanocrystalline materials preferably present crystallite sizes of less than about 25 nm, more preferably less 20 than nm, and most preferably less than 10 nm. The nanocrystalline particles preferably exhibit a Brunauer-Emmett-Teller (BET) multipoint surface area of at least about 15 m$^2$/g, more preferably at least about 70 m$^2$/g, and most preferably from about 100-850 m$^2$/g. Exemplary nanocrystalline materials are available from NanoScale Corporation, Manhattan, Kans., under the name NanoActive®.

In certain embodiments according to the invention, the nanocrystalline particles are contained in an air filtration device. In one embodiment, the nanocrystalline particles are present in the air filtration device in the form of a bed of particles. The particles may be packed together so as to form a packed bed, or loosely contained within a tray or other type of container. When arranged as a bed of particles, the air filtration device advantageously permits the particles to be exchanged from time to time so that fresh nanocrystalline particles may be present within the system.

FIG. 1 illustrates a portable air purifier 10 that utilizes a loose bed of particles 12. In this embodiment, purifier 10 comprises a housing 14 inside of which is a fan 16 that acts as the motive force for the movement of air into housing 14 and across particle bed 12. As used herein, the terms "fan" and "blower" essentially define any means acting as the motive force for the movement of air whether it is specific to a particular portion of the air handling system, or a part of equipment associated therewith or coupled thereto. As air moves across bed 12, the undesirable substances present within the air contact and are adsorbed by the nanocrystalline particles. Thus, the air exiting housing 14 is purified and is returned to the enclosed environment. Purifier 10 may be AC or DC powered. As shown, purifier 10 is powered by batteries 15. DC-powered versions of purifier 10 are particularly suited for use within small-volume enclosures such as refrigerators, freezers, automobiles, and closets. Larger, AC-powered portable purifiers are particularly useful in disaster recovery and restoration operations that require circulation of large volumes of air. Particularly, these larger units can be used in the clean up of fire, flood, and sewer damage within buildings. With a particle bed configuration, the spent particles can be replaced periodically with fresh particles. In alternate embodiments, particle bed 12 can be replaced with a cartridge containing the nanocrystalline particles. The cartridge can be similar in design to those cartridges described below or could be much simpler and comprise a disposable, porous bag or pouch containing the nanocrystalline particles.

Figure 2:
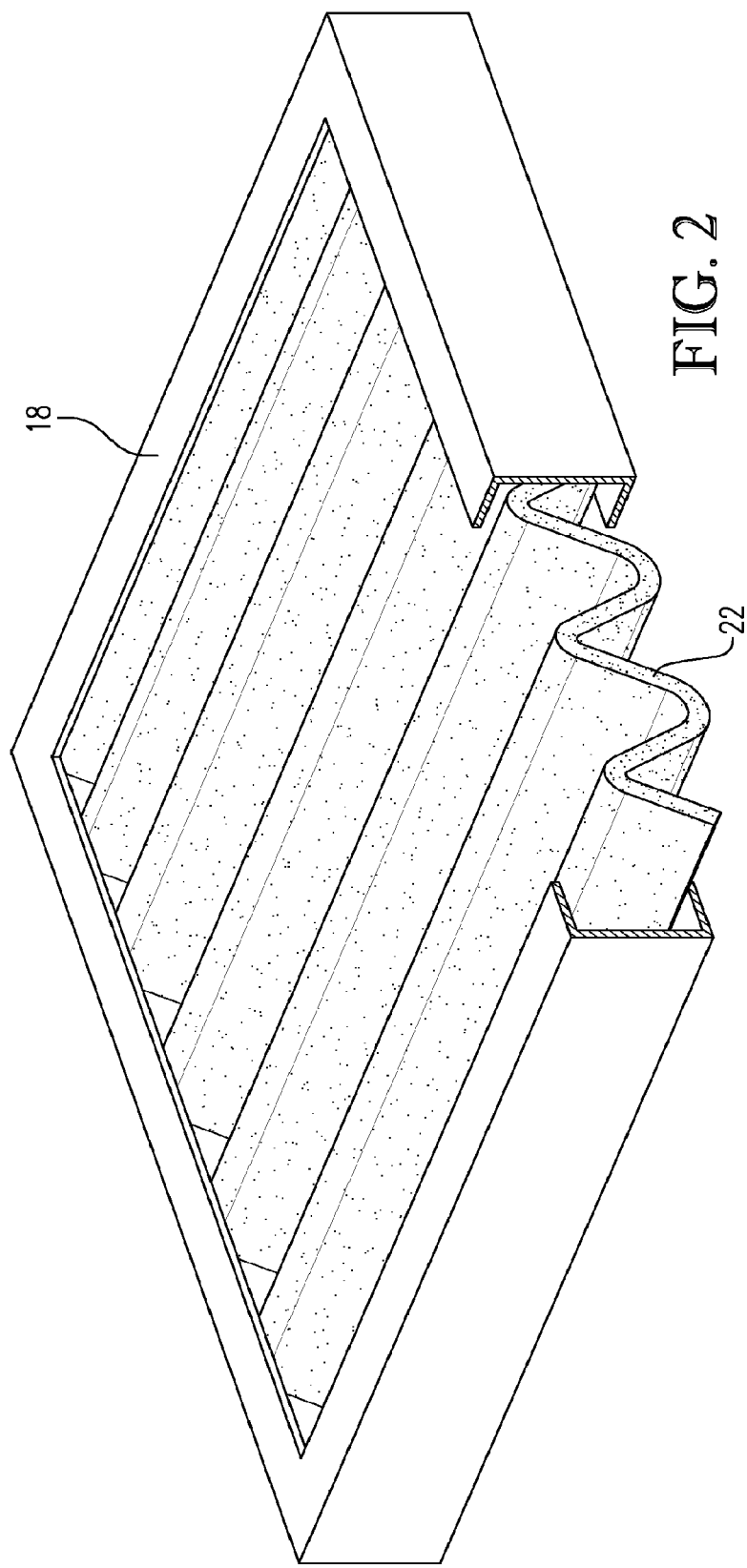
FIG. 2 is a view of a pleated filter cartridge having filter media which contains nanocrystalline metal oxide or hydroxide particles according to the present invention.
Figure 3:
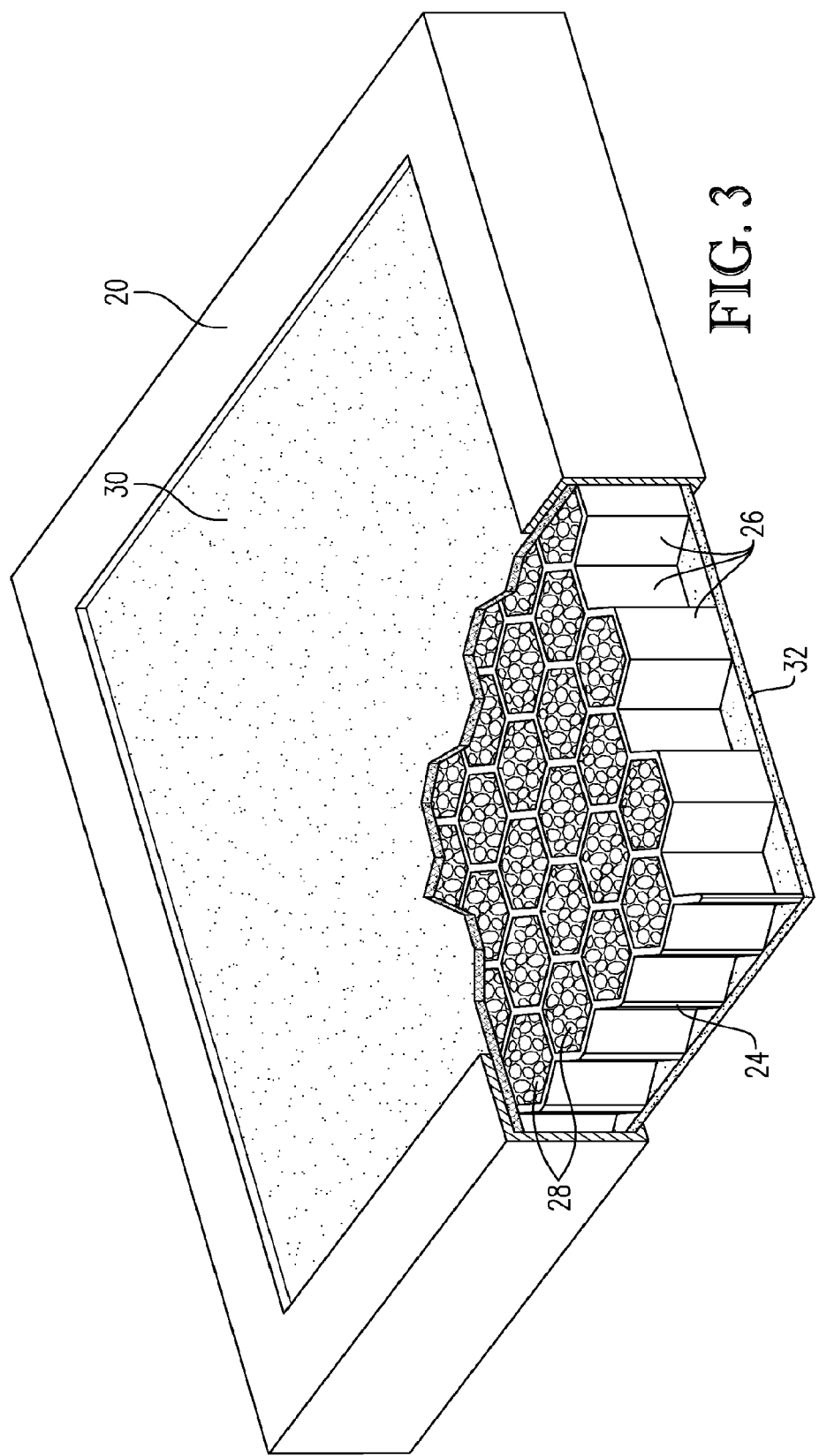
FIG. 3 is a view of a honeycomb-type filter cartridge having a plurality of cells filled with granulated metal oxide or hydroxide particles.

In another embodiment, the nanocrystalline particles are contained within a filter cartridge, such as cartridges 18 and 20 as shown in FIGS. 2 and 3, respectively. In one embodiment, filter cartridges 18 and 20 are interchangeable with a standard filter used in an air handling system, such as an HVAC system, a climate control system in a vehicle, train, or airplane, or portable air filtration device. One of skill in the art would recognize that the geometry of the filter cartridge could be altered to suit the required application, such as, for example, a canister-type filter, round filter, etc. The filter cartridge for use with the present invention generally comprises first filter media which contains the nanocrystalline particles. In alternate embodiments, the filter cartridges may comprise a second filter media for removing particulate matter from the air being circulated by the air handling system. The second filter media can be inter-dispersed with the first filter media or can be located entirely upstream or downstream therefrom. In certain embodiments, it is desirable to locate the second filter media upstream from the first filter media so that particulate matter circulating in the air can be removed prior to coming into contact with the first filter media containing the nanocrystalline particles, so as to avoid clogging or blocking air flow to the particles.

The first filter media may comprise a porous non-woven material in which the nanocrystalline particles are entrapped. The non-woven material may comprise a synthetic resin foam or film containing the nanocrystalline particles. Exemplary non-woven materials include natural fibers (e.g., cellulose, cotton, wool, etc.) and synthetic fibers (e.g., acrylic aromatic polyaramide, polyethylene, polypropylene, polyester, polimide, glass, polyphenylene sulfide, bi-component fibers, etc.). The second filter media may comprise the same or similar material as used in the first filter media. The second filter media may also contain nanocrystalline particles or it may not. Exemplary materials for use as the second filter media include natural fibers (e.g., cellulose, cotton, wool, etc.) and synthetic fibers (e.g., acrylic aromatic polyaramide, polyethylene, polypropylene, polyester, polimide, glass, polyphenylene sulfide, bi-component fibers, etc.).

As shown in FIG. 2, the filter cartridge 18 comprises a pleated sheet 22 of non-woven material into which the nanocrystalline particles are substantially uniformly distributed. As explained below, in numerous applications filter cartridge 18 is installed vertically within the air handling apparatus. Therefore, it is important that the nanocrystalline particles remain substantially uniformly distributed within the non-woven material and do not settle or migrate toward any particular area of the cartridge. In instances where nanocrystalline particles are dispersed within the fibers of conventional filter media, when the filter is installed vertically, the particles tend to settle toward the bottom of the filter cartridge, or into more dense pockets of particles disbursed at various locations within the media, thereby reducing their ability to contact the air moving through the cartridge. The present invention, however, solves this problem by entrapping the particles evenly throughout the media thereby maximizing the available surface area to come into contact with the circulating air.

In certain embodiments, the particles remain substantially uniformly distributed within the cartridge for a period of at least one month when the filter cartridge is vertically installed within the air handling apparatus. The ability to keep the nanocrystalline particles evenly distributed throughout the filter media even when installed vertically (as is the case for most filters used in conventional air handling systems) indicates that the nanoparticles are not simply applied as a loose powder to the filter. Rather, the particles and first filter media are formed in such a manner that the particles are entrapped and maintain a relatively constant local position within the filter media. In other embodiments, the first filter media comprises granules upon which the nanocrystalline particles are deposited as a coating. The granules may be nanocrystalline metal oxide/hydroxide particles themselves, or may another type of inert porous substrate such as activated carbon. The nanocrystalline particles may be applied to the granules as a plurality of coating layers in order to give a "time-release" odor-adsorbance effect wherein subsequent inner layers would gradually gain exposure to the air being circulated through the filter by the air handling apparatus.

FIG. 3 depicts an alternate embodiment of a filter cartridge made in accordance with the present invention. Cartridge 20 comprises a honeycomb-like structure 24 that includes a plurality of discrete cells 26 with each cell containing a quantity of granular nanocrystalline metal oxide or metal hydroxide material 28. The granules 28 are contained in the cells by first and second sheets 30, 32 of finely porous material. Sheets 30, 32 may comprise woven or non-woven materials that are sufficiently permeable to permit air to freely pass therethrough, but do not permit the granules 28 to escape cells 26. Thus, granules 28 are entrapped within cells 26 and remain substantially uniformly distributed throughout cartridge 20 even when vertically installed in air handling apparatus. Sheets 30, 32 may also be made of material similar to the above-described first and second filter media and be capable of filtering particulate matter from the air prior to passage through the honeycomb section 24.

In certain embodiments according to the present invention, the nanocrystalline particles are present in the air filtration device, or filter cartridge, at a loading of between about 50 g to about 1 kg per square foot (about 538 g to about 10.74 kg per square meter).

Thus, the filter according to the present invention performs the task of removing particles (i.e., dust, pet hair, lint, etc.) much as a conventional filter. However, unlike a conventional filter, the nanocrystalline particles contained by the first filter media also remove and neutralize undesirable chemical and biological substances present in the air, such as odors, bacteria, viruses, fungi, and toxins. Common odors that may be removed by the inventive filter cartridges include those caused by a member selected from the group consisting of urine, feces, sweat, decaying biological material, pesticides, organic solvents, volatile organic compounds, and combinations thereof. U.S. Patent Application Publication 2009/0098016, incorporated by reference above, discloses further exemplary odor-causing substances that may be removed by the nanocrystalline particles used with the present filter cartridge. Additionally, the nanocrystalline particles have the ability to remove harmful non-odorous materials and substances from air within the enclosed space. Exemplary materials and substances include HCN, CO, and biological species like viruses, bacteria, toxins and fungi.

Figure 4:
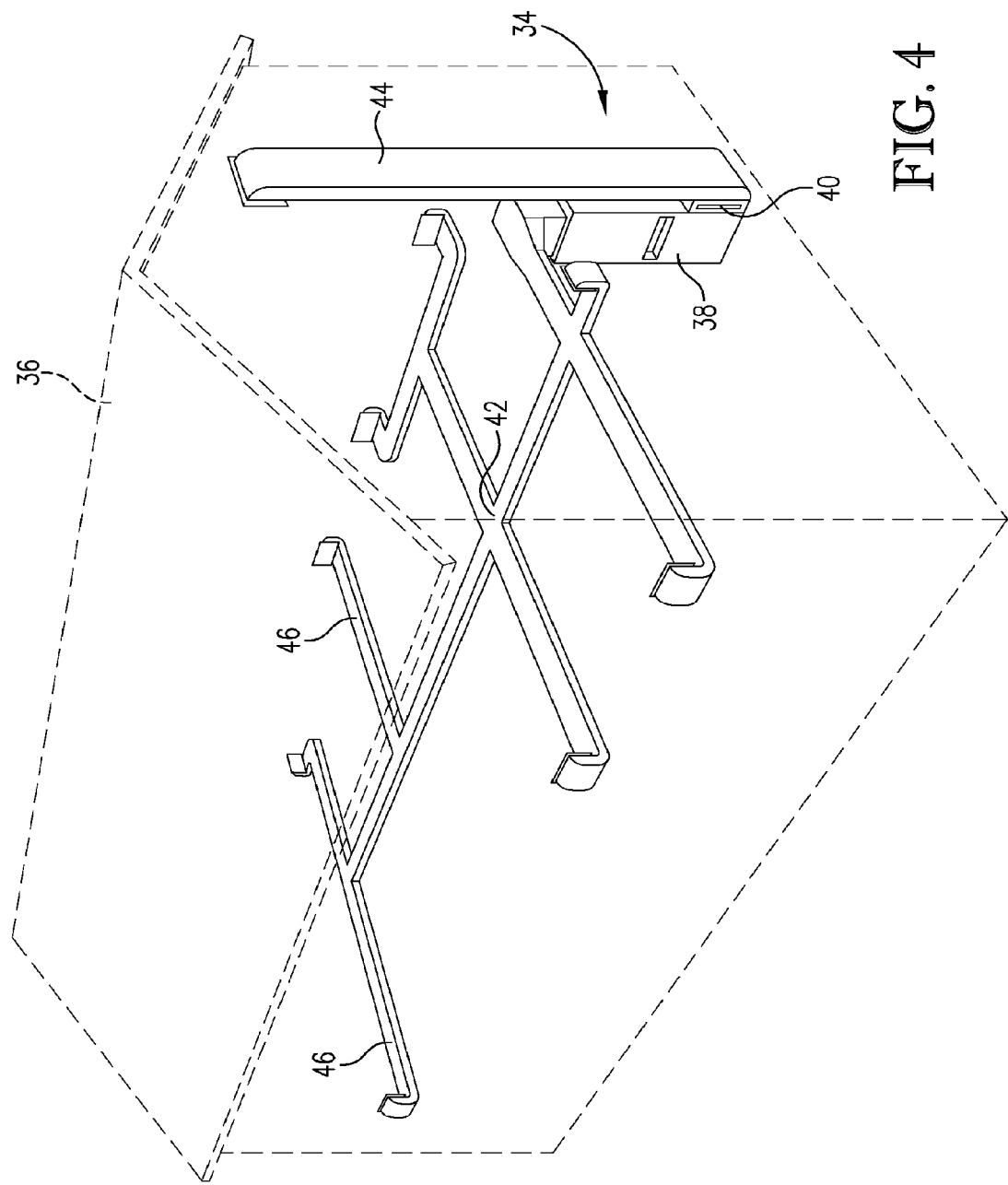
FIG. 4 is a schematic view of an HVAC system installed within a building with which the present invention may be used.

As discussed above, the filter devices, including the above-described filter cartridges 18, 20, are particularly suited for use with air handling apparatus, including fixed or permanently installed apparatus including HVAC systems, various vent systems such as hood vents and vents from industrial dryers and mixers. FIG. 4 depicts an exemplary air handling apparatus 34, particularly an HVAC system installed within a building 36 (e.g., a house, office building, industrial building, or warehouse), that includes a blower 38 acting as a motive force for circulating air within the enclosed environment and a filter cartridge 40. The HVAC unit generally comprises duct work 42 that directs the flow of air into and out of blower 38 for distribution within the building. At least one filter cartridge 40 is installed within the HVAC unit. Conventionally, apparatus 34 utilizes a cartridge primarily for particulate removal from the air passing through the air handling apparatus 34. However, in the context of the present invention, the cartridge containing the nanocrystalline particles may be installed in addition to or in place of the conventional filter (sometimes referred to as a furnace filter). The present filter cartridges are designed so as to minimize the pressure drop that occurs across the filter. Should a packed bed-type filter be used within air handling apparatus 34, a more powerful blower is needed in order to pull air through the filter and compensate for an increased pressure drop as most blowers installed in homes and various other types of buildings simply are not powerful enough to overcome the seemingly large pressure drop which occurs across a packed bed-type filter. But in certain applications, the use of a packed-bed filter is contemplated and may be highly practical. In alternate embodiments, however, the filter cartridges may be characterized as having much smaller pressure drops than conventional packed bed-type filters.

In certain embodiments, the filter is placed upstream of the HVAC's blower 38 so that the blower "pulls" air through the filter cartridge 40. Thus, air from within the building 36 is directed toward the blower 38 by way of one or more return-air ducts 44. The air from within the building 36 may be laden with odors or other undesirable substances present within the building structure. The blower 38 forces the air through the filter cartridge 40 where the undesirable substances are contacted with the nanocrystalline particles carried thereby. The undesirable substances are then sorbed onto the nanocrystalline particles, and a stream of purified air is directed through the blower 38 for distribution to the building via fresh air ducts 46.

Figure 5:
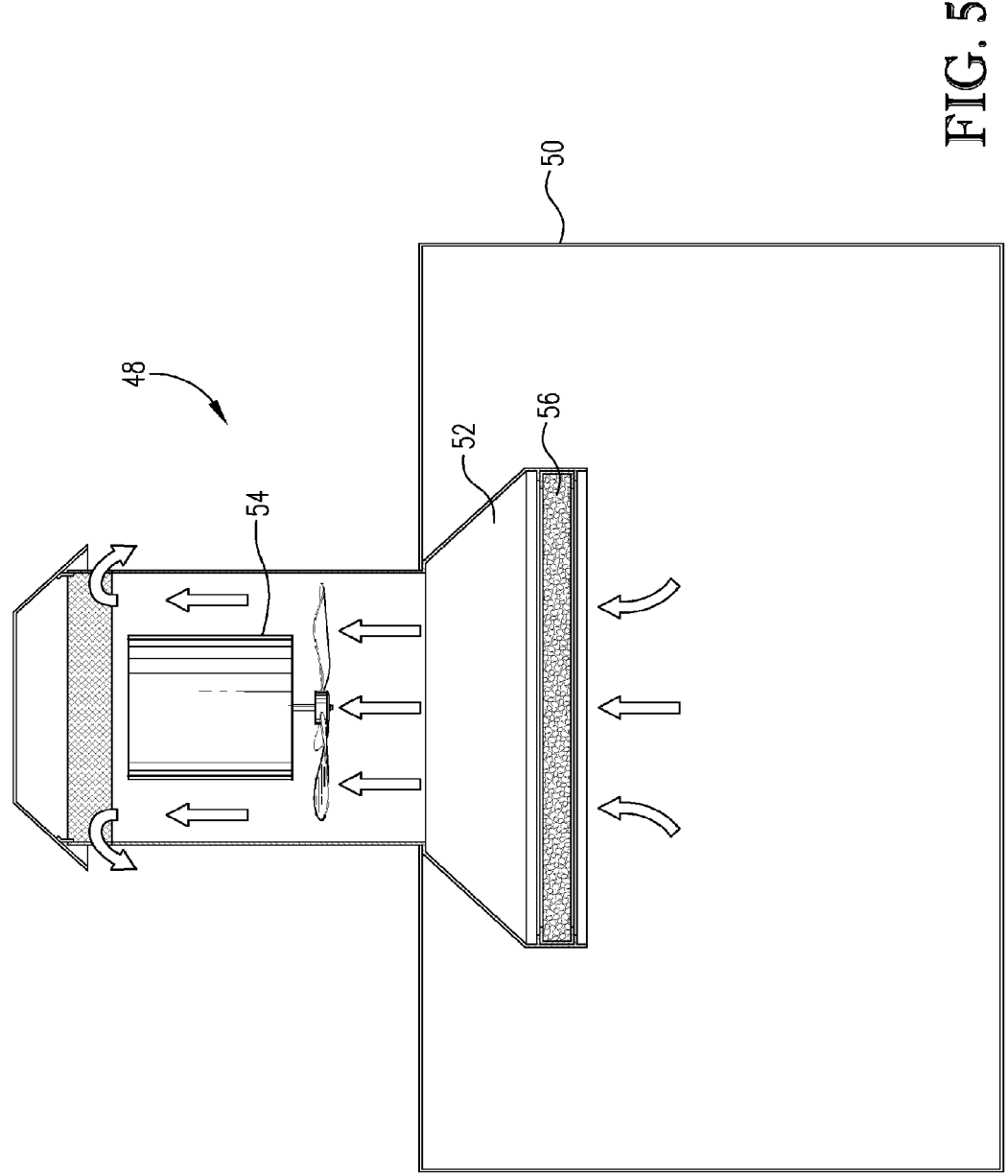
FIG. 5 is a schematic view of a ventilation system in which a portion of air passing through a filtration device in accordance with the present invention is vented outside of an enclosed environment.

FIG. 5 depicts an exemplary air handling system 48 in which at least a portion of the air passing through the system is vented outside of an enclosed space 50, such as to the atmosphere. The air handling system comprises a hood 52 and fan 54 that supplies a motive force for causing a flow of air containing one or more undesirable substances. Hood 52 is equipped with an air filtration device 56 such as any of those described above. Thus, air handling system 48 is operable to remove one or more undesirable substances, such as odors, bacteria, fungi, viruses, or toxins, from the air prior to being released into the atmosphere. It is understood that system 48 is merely exemplary of a system that is in communication with an enclosed space and also with the environment outside of the enclosed space, and that the present invention is not intended to be limited to only the apparatus shown. Rather, other types of venting systems utilizing the above principles can also be employed to remove undesirable substances carried by the air flow prior to the air being exhausted to the atmosphere.

As with other conventional filters, the filter cartridges according to the present invention may be replaced from time to time due to clogging of the various filter media, and due to saturation of the nanocrystalline particles carried by the first filter media. The useful service life for the filter cartridge may vary depending upon conditions existing with a particular building. For applications exhibiting large concentrations of suspended particulates or unusually strong odors or concentrations of undesirable substances, cartridge replacement will likely be needed more frequently. However, under normal conditions, the filter cartridge may continue to reduce or eliminate levels of odors and undesirable substances for at least one month, and preferably at least 3 months of substantially continuous operation of the air handling apparatus.

We claim:

1. A system for controlling and eliminating undesirable substances in an enclosed environment comprising:

an air handling apparatus including a blower which acts as a motive force for the flow of air within the enclosed environment; and an air filtration cartridge positioned so as to come into contact with the flow of air caused by said air handling apparatus, said filtration cartridge comprising a filter media, said filter media consisting essentially of:

(a) nanocrystalline particles consisting of metal oxides or metal hydroxides capable of removing one or more undesirable substances from the air flowing through said air handling apparatus, (b) one or more fibers selected from the group consisting of cellulose fibers, cotton fibers, wool fibers, polyethylene fibers, polypropylene fibers, polyester fibers, polyimide fibers, and glass fibers, and (c) optionally activated carbon.

2. The system according to claim 1, wherein said nanocrystalline particles are selected from the group consisting of oxides and hydroxides of Mg, Sr, Ba, Ca, Ti, Zr, Fe, V, Mn, Ni, Cu, Al, Si, Zn, Ag, Mo, Sb, Co, Cr and mixtures thereof.

3. The system according to claim 1, wherein said filter cartridge is removably inserted into said air handling apparatus.

4. The system according to claim 1, wherein said one or more fibers comprise a porous non-woven material, said nanocrystalline particles being entrapped within said non-woven material.

5. The system according to claim 4, wherein said non-woven material comprises a synthetic resin foam or film.

6. The system according to claim 1, wherein said filter media comprises granules upon which said nanocrystalline particles are deposited as a coating on said activated carbon.

7. The system according to claim 6, wherein said coating comprises a plurality of layers of said nanocrystalline particles.

8. The system according to claim 1, wherein said filter cartridge comprises a plurality of cells in which said nanocrystalline particles are contained.

9. The system according to claim 1, wherein said filter cartridge comprises a second filter media for removing particulate matter from the air flowing through said air handling apparatus.

10. The system according to claim 1, wherein said nanocrystalline particles are substantially uniformly distributed throughout said filter media, and remaining substantially uniformly distributed for a period of at least one month when said filter cartridge is vertically installed within said air handling apparatus.

11. The system according to claim 1, wherein said undesirable substance is selected from the group consisting of bacteria, fungi, viruses, toxins and odors, said odors being caused by a member selected from the group consisting of urine, feces, sweat, decaying biological material, pesticides, organic solvents, volatile organic compounds, and combinations thereof.

12. A method of controlling and eliminating undesirable substances from within an enclosed environment using an air handling apparatus including a blower which acts as a motive force for the flow of air within the enclosed environment being located within the enclosed environment, said method comprising the steps of:

providing an air filtration cartridge positioned so as to come into contact with the air flow generated by said air handling apparatus, said filtration cartridge comprising a filter media, said filter media consisting essentially of:

(a) nanocrystalline particles consisting of metal oxides or metal hydroxides capable of removing at least one undesirable substance from the air flowing through said air handling apparatus,
(b) one or more fibers selected from the group consisting of cellulose fibers, cotton fibers, wool fibers, polyethylene fibers, polypropylene fibers, polyester fibers, polyimide fibers, and glass fibers, and
(c) optionally activated carbon; and using said blower to direct air containing said at least one undesirable substance through said filtration cartridge in order to remove at least a portion of said at least one undesirable substance from the air thereby producing a flow of purified air.

13. The method according to claim 12, further comprising directing said purified air through said blower and into said enclosed environment.

14. The method according to claim 12, wherein said nanocrystalline particles are selected from the group consisting of oxides and hydroxides of Mg, Sr, Ba, Ca, Ti, Zr, Fe, V, Mn, Ni, Cu, Al, Si, Zn, Ag, Mo, Sb, Cr, Co and mixtures thereof.

15. The method according to claim 12, wherein said undesirable substance is selected from the group consisting of bacteria, fungi, viruses, toxins and odors, said odors being caused by a member selected from the group consisting of urine, feces, sweat, decaying biological material, pesticides, organic solvents, volatile organic compounds, and combinations thereof.

16. The method according to claim 12, wherein said one or more fibers comprise a porous non-woven material, said nanocrystalline particles being entrapped within said non-woven material.

17. The method according to claim 12, wherein said filter media comprises granules upon which said nanocrystalline particles are deposited as a coating on said activated carbon.

18. The method according to claim 17, wherein said coating comprises a plurality of layers of said nanocrystalline particles.

19. The method according to claim 12, wherein said filter cartridge comprises a plurality of cells in which said nanocrystalline particles are contained.

20. The method according to claim 12, further comprising the step of venting at least a portion of said purified air outside of said enclosed environment.

\* \* \* \* \*